United States Patent
Waksman (10) Patent No.: US 10,792,010 B2
(45) Date of Patent: Oct. 6, 2020

(54) MICROMANIPULATOR-CONTROLLED LOCAL VIEW WITH STATIONARY OVERALL VIEW

(71) Applicant: KONINKLIJKE PHILIPS N.V., Eindhoven (NL)

(72) Inventor: Peter Waksman, Concord, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 468 days.

(21) Appl. No.: 14/652,232

(22) PCT Filed: Nov. 20, 2013

(86) PCT No.: PCT/IB2013/060262
§ 371 (c)(1),
(2) Date: Jun. 15, 2015

(87) PCT Pub. No.: WO2014/097014
PCT Pub. Date: Jun. 26, 2014

(65) Prior Publication Data
US 2016/0183911 A1 Jun. 30, 2016

Related U.S. Application Data

(60) Provisional application No. 61/737,980, filed on Dec. 17, 2012.

(51) Int. Cl.
*A61B 8/08* (2006.01)
*A61B 5/06* (2006.01)
(Continued)

(52) U.S. Cl.
CPC .......... *A61B 8/0841* (2013.01); *A61B 5/06* (2013.01); *A61B 8/0883* (2013.01); *A61B 8/12* (2013.01);
(Continued)

(58) Field of Classification Search
None
See application file for complete search history.

(56) References Cited

U.S. PATENT DOCUMENTS 5,217,456 A 6/1993 Narciso
6,016,439 A * 1/2000 Acker ................. A61B 5/06
600/411

(Continued)

OTHER PUBLICATIONS

Pilu, G. et al, "Three-dimensional ultrasound examination of the fetal central nervous system", Ultrasound Obstet Gynecol. vol. 30, pp. 233-245, 2007.
(Continued)

*Primary Examiner* — Katherine L Fernandez
*Assistant Examiner* — Yi-Shan Yang (57) ABSTRACT

A tracking, and point-of-view-based imaging, device is configured for deriving a position of and a direction from, a location at a distal tip of an elongated instrument, for performing coordinate system transformation in accordance with the position and direction, and for forming, from the location and based on a result of the transformation, a local view that moves with the tip. The device can keep, with the movement, a field of view of the local view fixed but the local view otherwise in synchrony with the position and the direction. From real-time ultrasound imaging, the local view and a more overall view that includes the tip but which does not move with said tip can be displayed. The distal tip can be that of a catheter and can be outfitted with a micromanipulator for surgery aided interactively by the combination of dynamic local and overall imaging.

10 Claims, 7 Drawing Sheets

(51) Int. Cl.
*A61B 34/20* (2016.01)
*A61B 8/12* (2006.01)
*A61B 8/00* (2006.01)
*A61B 90/00* (2016.01)

(52) U.S. Cl.
CPC .............. *A61B 8/445* (2013.01); *A61B 8/463* (2013.01); *A61B 8/469* (2013.01); *A61B 8/5223* (2013.01); *A61B 34/20* (2016.02); *A61B 2034/2051* (2016.02); *A61B 2034/2063* (2016.02); *A61B 2090/3782* (2016.02)

(56) References Cited

U.S. PATENT DOCUMENTS

| | | | |
|---|---|---|---|
| 6,226,547 | B1 | 5/2001 | Lockhart |
| 6,778,689 | B1 * | 8/2004 | Aksit .................... A61B 5/055 382/128 |
| 6,896,657 | B2 | 5/2005 | Willis |
| 8,073,215 | B2 | 12/2011 | Lu |
| 8,303,505 | B2 * | 11/2012 | Webler ............... G06F 19/3437 600/437 |
| 8,517,923 | B2 | 8/2013 | Belson et al. |
| 2005/0143651 | A1 * | 6/2005 | Verard .................. A61B 34/20 600/424 |
| 2005/0238218 | A1 | 10/2005 | Nakamura |
| 2007/0167801 | A1 * | 7/2007 | Webler .................... G06T 19/00 600/459 |
| 2009/0105579 | A1 * | 4/2009 | Garibaldi ........... A61B 1/00158 600/409 |
| 2009/0118620 | A1 | 5/2009 | Tgavalekos |
| 2010/0041949 | A1 | 2/2010 | Tolkowsky |
| 2010/0268067 | A1 * | 10/2010 | Razzaque ............ A61B 8/4245 600/424 |
| 2011/0060209 | A1 * | 3/2011 | Shikata ................ A61B 1/3132 600/407 |
| 2012/0046521 | A1 | 2/2012 | Hunter |
| 2012/0203296 | A1 | 8/2012 | Lisogurski |
| 2013/0096575 | A1 * | 4/2013 | Olson .................. G06T 19/003 606/130 |
| 2013/0150710 | A1 * | 6/2013 | Zentgraf ................ A61B 8/461 600/424 |
| 2014/0330128 | A1 * | 11/2014 | Sakaguchi ........... A61B 8/4245 600/472 |

OTHER PUBLICATIONS

Kupesic, S. et al "Clinical Application of 3D Sonography", CRC Press, 2000, pp. 222-223.

* cited by examiner

MICROMANIPULATOR-CONTROLLED LOCAL VIEW WITH STATIONARY OVERALL VIEW

CROSS-REFERENCE TO PRIOR APPLICATIONS

This application is the U.S. National Phase application under 35 U.S.C. § 371 of International Application No. PCT/IB2013/060262, filed on Nov. 20, 2013, which claims the benefit of U.S. Provisional Patent Application No. 61/737,980, filed on Dec. 17, 2012. These applications are hereby incorporated by reference herein.

FIELD OF THE INVENTION

The present invention relates to tracking an object and to local imaging from the object and, more particularly, to local imaging from a location on the object.

BACKGROUND OF THE INVENTION

Ultrasound-assisted surgery using three-dimensional (3D) ultrasound images is developing rapidly, with advances in transducer technology being paralleled by advances in catheter technology.

Minimally invasive intravascular surgery can be performed using a variety of possible devices disposed at the distal end of a catheter. The clinician advances the catheter into the body through an incision and up through a vein. Control exists at the proximal end, as on a handle, for steering the catheter through a tortuous path. At the destination, the device (or "micromanipulator") is manipulated proximally to carry out the surgical procedure. Other types of surgical procedures carried out by means of a catheter are laparoscopy, thoracoscopy, pleuroscopy, atherectomy, laser ablation, etc.

U.S. Pat. No. 6,226,547 to Lockhart et al. (hereinafter "Lockhart") discloses using a magnetic field to track a catheter. Lockhart displays the location of the catheter's head, but does not mention imaging.

U.S. Patent Publication No. 2009/0118620 to Tgavalekos et al. (hereinafter "Tgavalekos") discloses an ablation catheter, and an imaging catheter for monitoring the ablation. Both catheters are magnetically tracked, and respective representations are superimposed, for display, on pre-operative or intra-operative imaging of the region undergoing ablation. The imaging is driven by a motor. To avoid motor noise interference with the tracking, multiple tracking devices are placed together on the imaging catheter.

U.S. Pat. No. 5,217,456 to Narciso, Jr. (hereinafter "Narciso") is configured for imaging from the catheter distal tip by means of light carried on an optical fiber, the light entering and exiting through an axially rotating side-looking window.

SUMMARY OF THE INVENTION

Aspects of the present invention are directed to addressing one or more of the shortcomings noted above with regard to the prior art.

None of the above-referenced documents, each of which is incorporated herein by reference in its entirety, offers a sufficient solution on how to safely, robustly and easily monitor catheter-based surgery.

At present, no simple, effective, minimally-invasive means exists for providing image guidance during surgery that is performed by means of a catheter.

In particular and by way of example, the design of the imaging catheter in Tgavalekos is complicated by the need for the multiple tracking devices. Also, there is no local imaging from the point of view of the ablation catheter tip. Nor is there any such imaging that dynamically moves with the tip to thereby, in concert with an overall view, relieve the surgeon from operating the imaging controls during the procedure. Nor is there any such imaging that offers the advantages of ultrasound in differentially imaging soft tissue.

Additionally, although some catheters for surgery include a local imaging device at the distal tip, as in Narciso, it is burdensome to include all the functionality needed at the tip, e.g., the imaging device, micromanipulator, cooling mechanism in the case of thermal ablation, and steering cable connections.

In an aspect of the present invention, a tracking, and point-of-view-based imaging, device is configured for deriving a position of, and a direction from, a location at a distal tip of an elongated instrument. It is further configured for performing coordinate system transformation in accordance with the derived position and derived direction, and for forming, from the location and based on a result of the transformation, a local view that moves with the tip.

As a sub-aspect, the instrument serves as a component of the device.

In a further sub-aspect, the instrument is outfitted for delivering, at the tip, medical treatment and/or a medical apparatus.

In a related sub-aspect, the tip is configured specifically for manipulating body tissue for a medical purpose.

In a yet further related sub-aspect, the instrument includes a catheter. The tip is disposed intracorporeally.

In another sub-aspect, the device is configured for keeping, with the movement, a field of view of the local view fixed but the local view otherwise in synchrony with the position and the direction.

As an alternative sub-aspect, the device is further configured for dynamically detecting an update in the position and/or direction and for repeating, dynamically in response to the detecting of an update, the deriving, the performing and the forming.

In a supplementary aspect, the device, further configured for real-time imaging, includes a display. The device is further configured for displaying, on the display and from the real-time imaging, the local view and a more overall view that includes the tip but which does not move with the tip.

As a particular sub-aspect, the device is further configured for repeating as an update, at least once per second, the deriving, the performing and the forming.

In a specific sub-aspect, the device is further configured for real-time ultrasound imaging, and the forming is based on data acquired in the real-time ultrasound imaging.

As a further sub-aspect, the forming is based on data acquired in the real-time imaging of the tip.

In a still further sub-aspect, the deriving entails determining the position and/or direction based on content of the imaging of the tip.

In one particular sub-aspect, the deriving of direction includes doing so from the real-time imaging of structures at the tip.

It is also a sub-aspect that the device further includes a display and is configured for displaying the local view on the display.

As a further sub-aspect, the device is further configured for real-time imaging and for switching between the local view and a more overall view that is formed from the real-time imaging.

In a yet further sub-aspect, the switching is responsive to user actuation of a control.

In an alternative sub-aspect, the device is further configured for real-time imaging and for simultaneously displaying the local view and a more overall view that is formed from the real-time imaging.

As one other sub-aspect, the device further includes a display, and is further configured for real-time imaging and for displaying, from the real-time imaging, a more overall view that includes the tip but which does not move with the tip.

In one exemplary sub-aspect, the device includes a transesophageal echocardiography (TEE) probe configured for outputting information from which the forming occurs.

In an additional sub-aspect, the location moves with, but is fixed with respect to, the tip.

In one other aspect, the device is configured for adjusting the transformation by conforming an orientation about an axis in the direction with feedback from the facility.

With such a system, the surgeon can switch between a "landscape" view of the heart including the manipulator (like "birds-eye view" in a computer game) versus a "local" view (like "avatar view" in a computer game) showing the part of the heart directly in front of the manipulator. It is believed that the computer game metaphor is meaningful—these two types of views have evolved as the most desirable views during an action game—which has a lot of similarity to the activity during a cardiac intervention surgery. Alternatively we could consider the metaphor of finding your way through a cave—a map of the cave (landscape) and a flashlight (local) are both useful—not one or the other.

The general problem is to support hand-eye coordination of the surgeon during ultrasound-assisted cardiac intervention procedures. But in particular, what is proposed herein addresses the problem of providing both a local view and a landscape view of the region of the heart being operated on. The local view is used for performing the procedure. The landscape view is used for positioning the micromanipulator catheter. Hence a good system should provide both.

Details of the novel, tracking, and point-of-view-based imaging, device are set forth further below, with the aid of the following drawings, which are not drawn to scale.

DETAILED DESCRIPTION OF EMBODIMENTS

Figure 1:
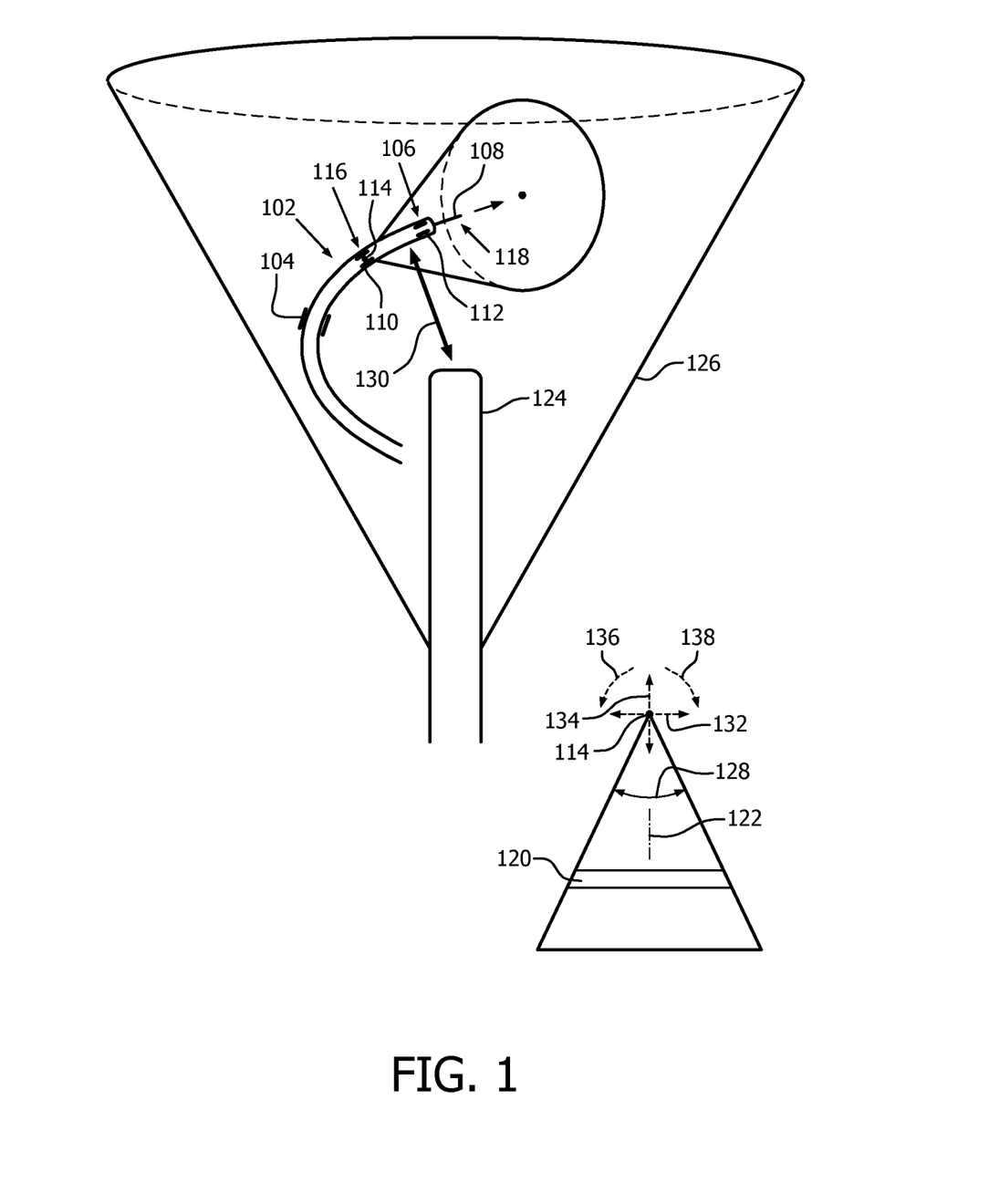
FIG. 1 is a schematic and conceptual diagram of surgical-instrument tracking and point-of-view-based imaging in accordance with the present invention.

FIG. 1 depicts exemplary surgical-instrument tracking and point-of-view-based imaging.

The body of an elongated surgical instrument 102, such as a catheter for internal use, is shown disposed within a blood vessel 104 or organ cavity. At the distal tip 106 of instrument 102 is an electrode 108, for ablation or electrophysiology for example. The electrode 108 may be retractable and extendable. The retraction/extension and steering are controlled proximally at a handle (not shown) of the instrument 102. Also at the distal tip 106 are two echoic structures 110, 112 usable for ultrasonically tracking the tip. The structures 110, 112 may be hollowly annular and radially symmetric. The hollowness keeps free the axial center of the catheter body, for functions like stent advancement. The symmetry aids in identifying the center of each structure 110, 112. For instance, a position 114 of a location 116 at the distal tip 106 is central within the proximal structure 110, and a local viewing direction 118 from the location corresponds to a line from the location to the center of the distal structure 112. A local view 120 is from that location 116 and in the local viewing direction 118. The local view 120 is reconstructed from live imaging, as discussed in detail further below. Associated with the local view 120 is an orientation of the tip 106 about an axis 122 in the local viewing direction 118. The orientation is relevant for a catheter that, for example, has, for steering, a "left" pull wire and a "right" pull wire, as also discussed in more detail further below. One or both of the structures 110, 112 at the tip 106 may be circumferentially non-symmetrical to facilitate ultrasonic determination of the orientation. Alternatively, the distal tip 106 could include one or more magnetic field transducers for tracking as in Lockhart and Tgavalekos. Although the local viewing direction 118 is shown in FIG. 1 to be longitudinally straight ahead from the distal tip 106, it may alternatively be in another direction, such as a side-looking direction.

A transesophageal (TEE) probe 124 is shown, by way of illustrative and non-limitative example, with forward-looking optics, such as those commonly provided for intravascular ultrasound (IVUS) catheters. However, the optics may instead, or in addition, include side-looking capability. TEE volumetric data 126 acquisition is in real time. The live imaging includes imaging of the distal tip 106 and surrounding anatomy.

From a subset of the data 126, the local view 120 is formed whose field of view (FOV) 128 is denoted in FIG. 1 by the angular range shown. The local view 120 depicted in FIG. 1 is formed from real-time C-plane imaging, although any subset, thick or thin, of the data 126 may constitute the local view. Forming the local view 120 entails a coordinate system transformation 130 of at least the corresponding TEE volumetric data 126 to the local view. The local view 120 moves with the distal tip 106, with the FOV 128 remaining fixed. The FOV 128 is shown in FIG. 1 to be about 30 degrees, but any angular sector could be used. The movement can be translational as seen from the orthogonal broken double-headed straight arrows 132, 134 in FIG. 1. The third orthogonal direction is another type of movement, but is not shown in FIG. 1. The movement can also be rotational, as seen from the pair of curved arrows 136, 138, although, in the two other orthogonal orientations, rotations in either direction are possible. Thus, the movement of the local view 120, as a result of operation of the catheter controls in the handle, can be likened to moving a flashlight in one's grasp. For clinical interventions, the local view 120 is best used in conjunction with a more overall view that includes the catheter distal tip 106 and surrounding anatomy, for example a live image of the heart.

Figure 2:
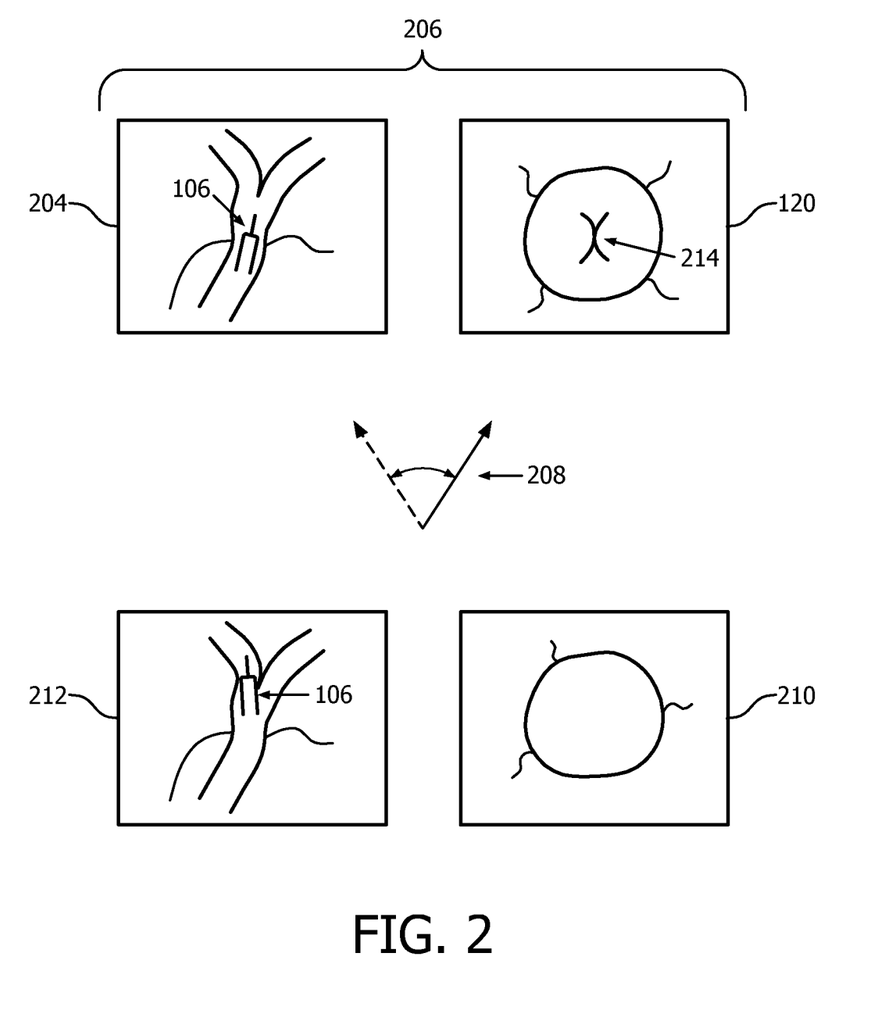
FIG. 2 is a conceptual diagram of possible display screen snapshots and configurations in accordance with the present invention.

The local view 120 in FIG. 2 is seen on a display, accompanied by a more overall or global view 204. The bracket 206 in FIG. 2 signifies that the two views 120, 204 appear simultaneously. The surgeon need merely switch his or her gaze between the two views 120, 204 in performing the surgical procedure. Concurrently, the surgeon manually operates user controls on the catheter handle to operate the micromanipulator situated at the catheter's distal tip 106. Both views 120, 204 are preferably updated in real-time, i.e., at least once per second or at another frequency such as between 20 and 60 Hz. As an alternative, the views 120, 204 can alternate onscreen as indicated in FIG. 2 by the sector-sweeping arrow configuration 208, optionally each view sized for filling up available screen space. Each alternation can be user-actuated as by a toggle switch, or automatic without user intervention. With user actuation, the clinician's hands can be kept free for the surgery if a foot pedal is used. The toggle switch could instead reside on the catheter handle. Whether the switch is on the catheter handle or elsewhere such as on the ultrasound console, if switching is done manually, this can be done at a convenient time during the surgery—the surgeon is still relieved of having to operate ultrasound controls responsive to imaging changes that accompany movement of the distal tip 106.

As temporal updates, a local view 210 and simultaneous more overall view 212 show that the local view moves with the distal tip 106 whereas the more overall view does not. Here, as seen from comparing the two overall views 204, 212 the distal tip 106 moves into one of two branches of the blood vessel 104, but the view has not moved. On the other hand and correspondingly, a branching point 214 seen at the earlier time in the local view 120 is no longer visible, as the distal tip 106 has entered the left-hand branch and offers now the new local view 210.

Figure 3:
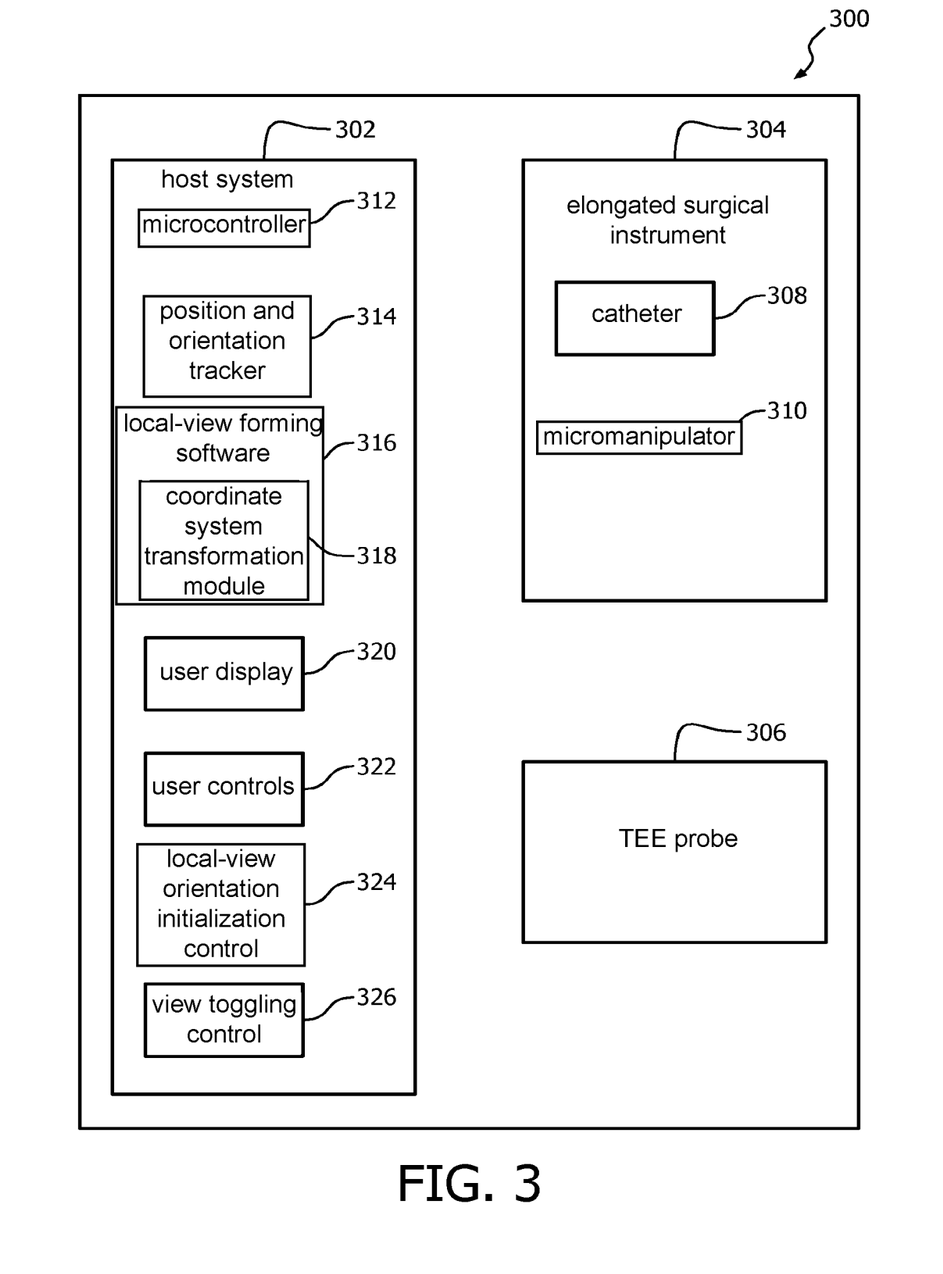
FIG. 3 is a structural and functional overview diagram of a surgical-instrument tracking, and point-of-view-based imaging, device in accordance with the present invention.

FIG. 3 provides an overview of a particular, exemplary surgical-instrument tracking, and point-of-view-based imaging, device 300. It includes a host system 302 and an elongated surgical instrument 304. It further includes a transesophageal (TEE) probe 306 having a 2D ultrasound transducer, and a beamformer, for real-time 3D imaging.

The elongated surgical instrument 304 is made up of a proximal handle and an elongated body. The elongated body includes a catheter 308 and, at the distal tip 106 of the catheter, a micromanipulator 310 such as a pair of scissors or plyers, a stent placement mechanism, or any other device. More generally, the distal tip 106 can be designed for manipulating or transforming body tissue. Or, it can be designed merely, or in addition, for monitoring through some type of sensing, for dispensing a substance, endogenous or exogenous, such as a medicine, chemical or agent, or it can be designed for any other medical use.

The host system 302 includes a microcontroller 312, a position and orientation tracker 314, local-view forming software 316 that includes a coordinate system transformation module 318, and a console. The console features a user display 320 such as a screen for presenting images, and user controls 322 for imaging which include a local-view orientation initialization control 324 and a view toggling control 326. The position and orientation tracker 314 uses the volumetric data acquired in real time by the TEE probe 306 to localize the echoic structures 110, 112 at the tip 106 of the catheter 308. Alternatively, other tracking methods may involve one or more magnetic field transducers at the catheter tip 106, and a reference tracking element which may be introduced into the patient by means of a separate catheter, as described in Tgavalekos. In this case, the reference tracking element would be communicatively coupled, wirelessly or by wireline, to the tracker 314 in the host system 302. The host system 302 can be realized in software, hardware, firmware or any combination thereof.

In some embodiments, such as a movement-dependent embodiment of the device 300 discussed further below, the microcontroller 312 can be designed to exchange signals with an electronic control in the handle of the catheter 308. For some embodiments, the microcontroller device 312 can be implemented as one or more integrated circuits.

Figure 4A:
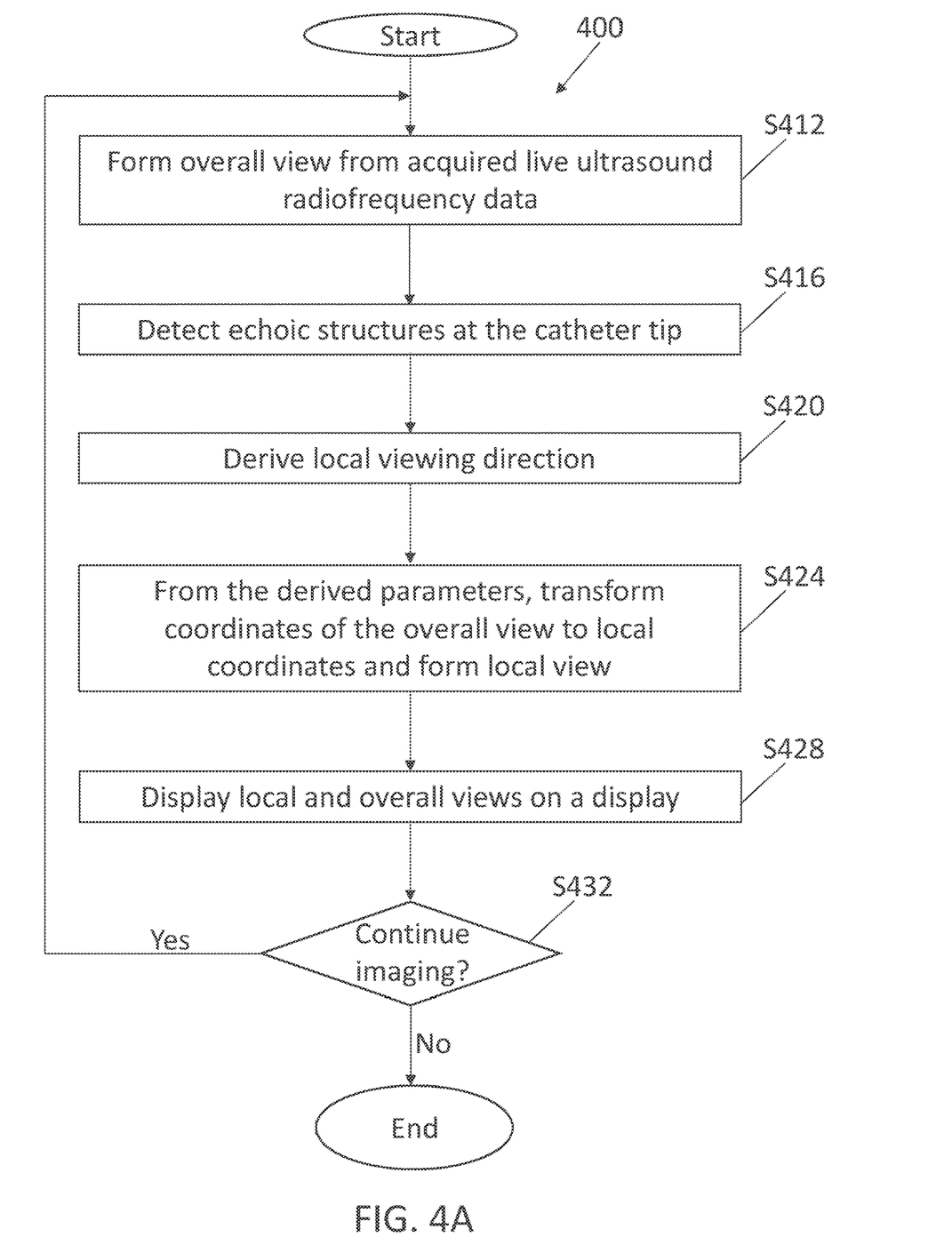
FIGS. 4A, 4B, 4C are alternative flow charts of tracking and point-of-view-based imaging in accordance with the present invention.
Figure 4B:
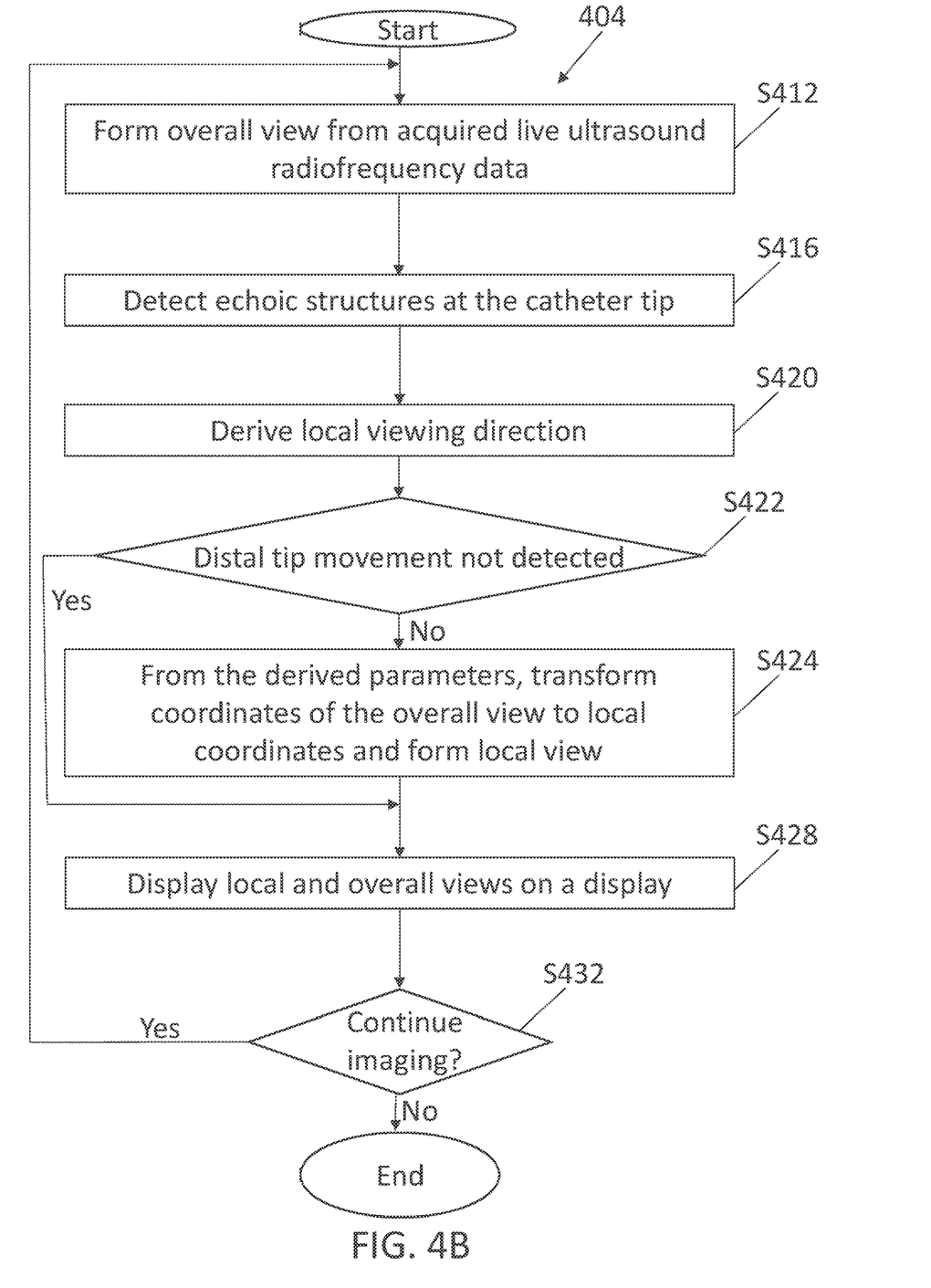
Figure 4C:
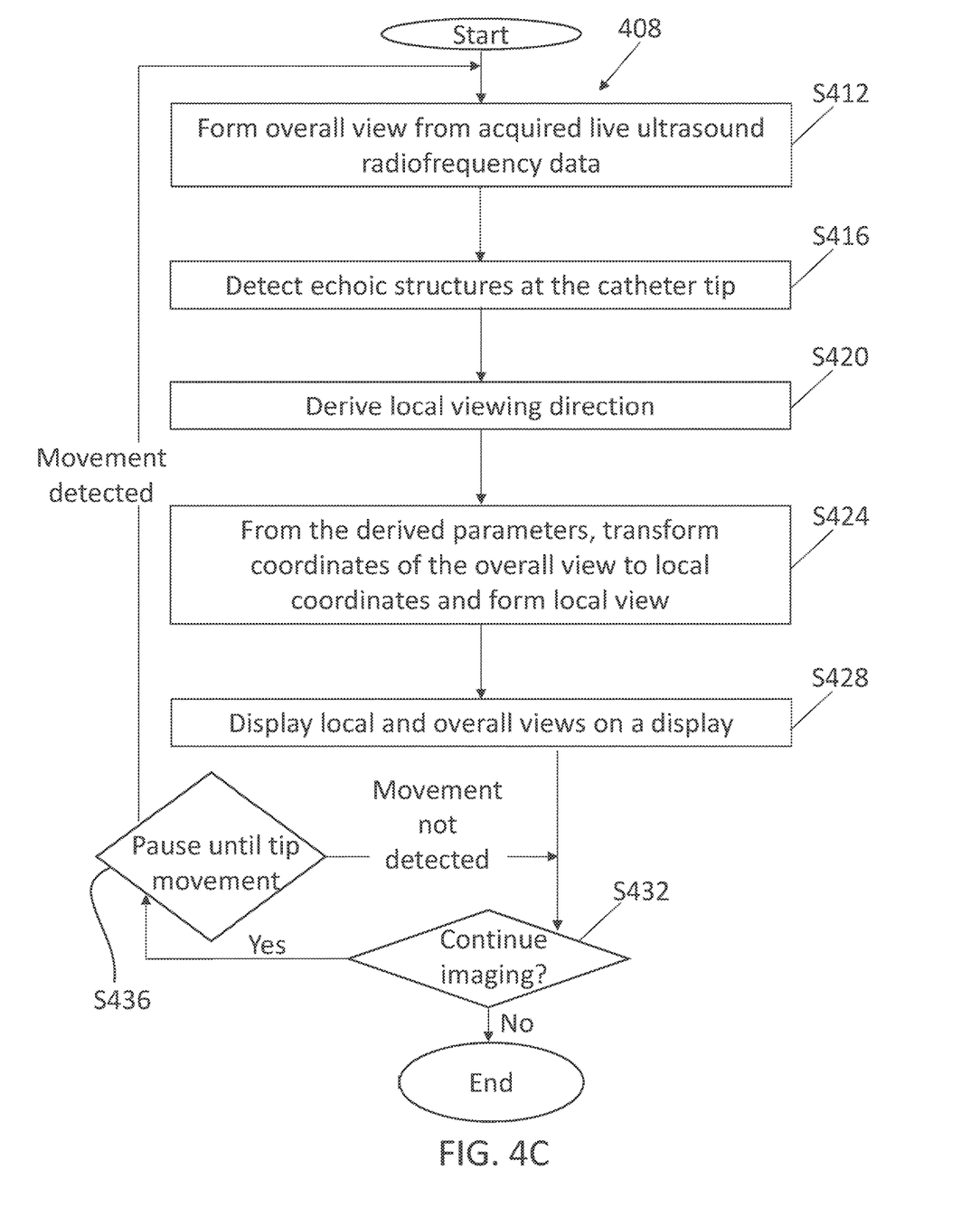

Referring to FIGS. 4A, 4B, 4C, track and point-of-view-based imaging is realizable according to a movement-independent process 400 or alternative, movement-dependent processes 404, 408. The processes 400, 404, 408 are managed by the microcontroller 312 in the host system 302.

For the movement-independent process 400, the overall view 204 is formed from acquired live ultrasound radiofrequency (RF) data (step S412). The overall view 204 is associated with a specific geometric configuration that constitutes a volumetric set of RF data. The configuration may be confined to an organ such as the heart or portion of the heart. From the overall view 204, the echoic structures 110, 112 at the catheter tip 106 are detected (step S416). From the proximal one 110 of the structures, the position 114 is derived, and from both structures 110, 112, the local viewing direction 118 is derived (step S420). The echogenecity of structures is such that their brightness is automatically distinguishable. The distinguishing is done, by the position and orientation tracker 314, in the imaging that constitutes the overall view. The structures 110, 112 could each be annular, gas-filled gaps sandwiched within the walls of the catheter 308. To complement the position 114 and direction 118, the orientation of the tip 106 may also be derived. However, the orientation of the catheter may not be needed or desired, in which case any arbitrary orientation can be supplied for coordinate system transformation purposes. As noted herein above, an alternative to implementing the echoic structures 110, 112 is electromagnetic tracking. The results of which are derived by the host system 302. The derivation occurs by virtue of reception from a discrete tracking facility. Or, the derivation occurs as a result of calculations performed by the position and orientation tracker 314 based on input from the reference tracking element. From the derived parameters, coordinates of the overall view 204 are transformed to local coordinates by the coordinate system transformation module 318 of the local-view forming software 316. This forms the local view 120 (step S424). The local and overall views 120, 204 are displayed on the display 320 (step S428). If imaging is to continue (step S432), processing returns to step S412. As mentioned above, the process 400 can operate in real time, iterating at least once per second.

The first movement-dependent process 404 is similar, but includes a conditional branch between the third and fourth steps S420, S424. If movement of the distal tip 106 is not detected (step S422), processing skips the coordinate transforming step S424 to display the local and overall views 120, 204 (step S428). Tip movement is detected if either the position 114, the direction 118, or the orientation has changed since the previous iteration.

The second movement-dependent process 408, by means of step S436, conditionally pauses the process after the last step S432 until tip movement is detected. Tip movement in this process 408 is detected by means of the user controls in the handle of the catheter 308. The handle controls are communicatively coupled, wirelessly or by wireline, to the microcontroller 312 in the host system 302.

Figure 5:
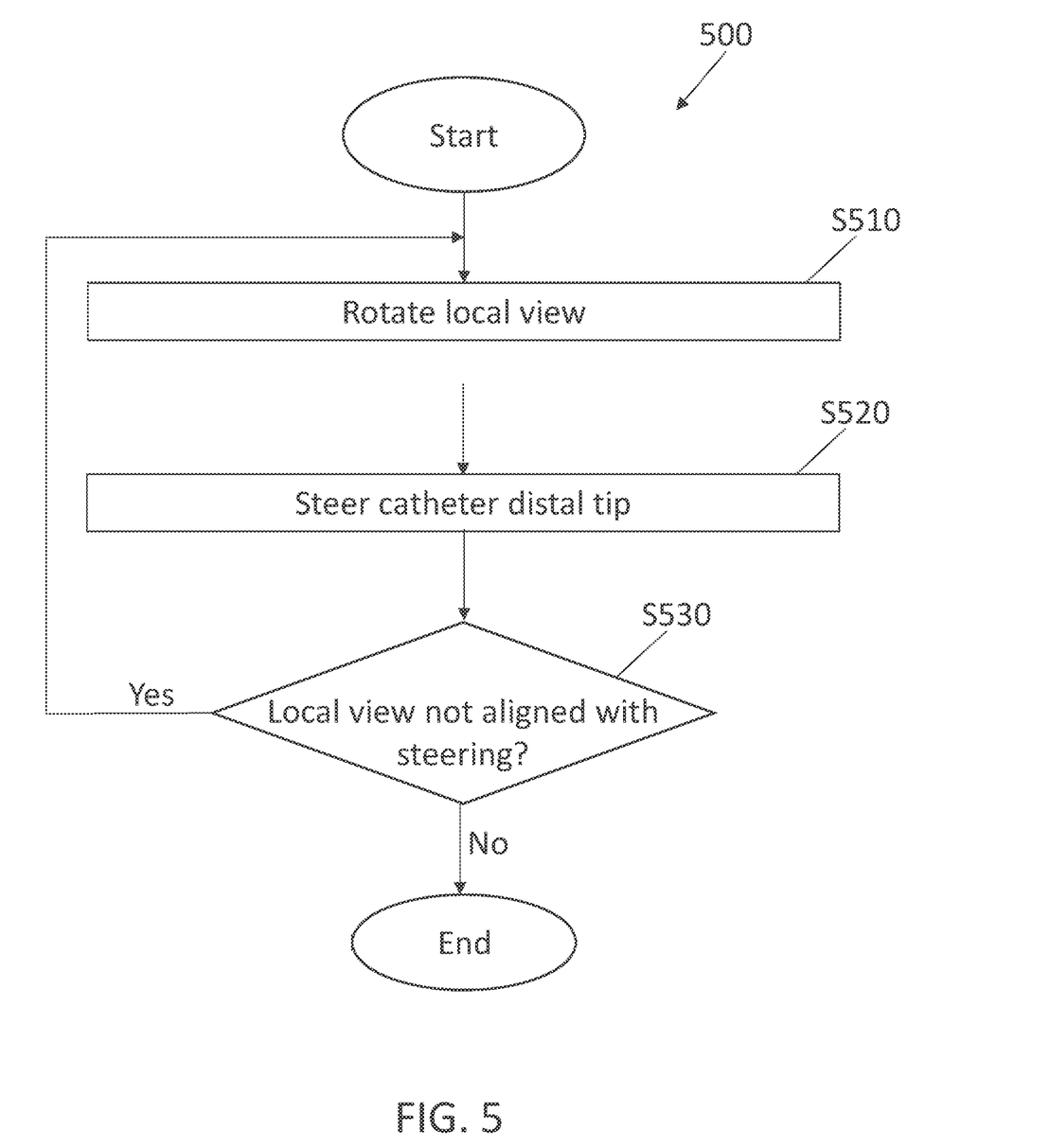
FIG. 5 is a flow chart of local-view display initialization in accordance with the present invention.

An optional, local-view display initialization process 500 is exemplified in FIG. 5. In this embodiment, the surgical-instrument tracking, and point-of-view-based imaging, device 300 features a steering facility for the elongated surgical instrument 304 and is configured for adjusting the transformation by conforming an orientation about an axis in the direction 118 with feedback from the facility. This embodiment is intended for when the user needs or desires the orientation, e.g., so that the local view 120 displayed features rightward motion when pulling on the "right" catheter steering cable and leftward motion when pulling on the "left" steering cable. Operationally, a user manipulates the local-view orientation initialization control 324, by means of an onscreen slide bar for example, interactively to rotate the local view 120 (step S510). This involves the local-view forming software 316 adjusting the transformation according to the user-induced rotation. The user then tests the rotational alignment by operating the catheter handle to slightly steer the catheter distal tip 106 (step S520). If the user sees onscreen that the local view 120 is not yet aligned with the steering (step S530), return is made to step S510; otherwise, alignment is complete.

A tracking, and point-of-view-based imaging, device is configured for deriving a position of, and a direction from, a location at a distal tip of an elongated instrument, for performing coordinate system transformation in accordance with the position and direction, and for forming, from the location and based on a result of the transformation, a local view that moves with the tip. The device can keep, with the movement, a field of view of the local view fixed but the local view otherwise in synchrony with the position and the direction. From real-time ultrasound imaging, the local view and a more overall view that includes the tip but which does not move with said tip can be displayed. The distal tip can be that of a catheter and can be outfitted with a micromanipulator for surgery aided interactively by the combination of dynamic local and overall imaging.

Applications of the tracking, and point-of-view-based imaging, device include cardiac intervention and other ultrasound-assisted surgeries that use a micromanipulator.

While the invention has been illustrated and described in detail in the drawings and foregoing description, such illustration and description are to be considered illustrative or exemplary and not restrictive; the invention is not limited to the disclosed embodiments.

For example, although a stationary TEE probe is used in the illustrative embodiments, a stationary transthoracic echocardiography (TTE) probe may instead be utilized. Also, although a catheter, such as a cardiac catheter is the elongated instrument used in the illustrative embodiments, other elongated instruments such as a laparascope, endoscope, colonoscope or speculum are within the intended scope of what is proposed herein above. Nor is what is proposed herein above confined to treatment or diagnosis; for example, tracking and point-of-view-based imaging may be used in an autopsy, with the micromanipulator moving tissue to reveal a structure.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. A tracking and imaging system comprising:
an elongated instrument configured for insertion into a target site, the elongated instrument comprising a distal tip and an echoic structure located on the distal tip;
a probe positioned external to the target site configured to acquire volumetric data from the target site and detect the echoic structure; and
a processor configured to:
generate a global view of the target site using the volumetric data acquired in real time by the probe;
determine a position and an orientation of the distal tip based at least in part on the position and the orientation of the echoic structure;
reconstruct a local view from a point of view of the distal tip by transforming a subset of the volumetric data acquired in real time by the probe into local volumetric data at the position of the distal tip and in a local viewing direction that is based on the orientation of the distal tip;
reconstruct an updated local view when a change in the position or the orientation of the distal tip within the target site is detected; and
pause the reconstruction of the local view when no change in the position or orientation of the distal tip is detected.

2. The system of claim 1, wherein the distal tip comprises a micromanipulator configured for manipulating body tissue at the target site during a medical procedure.

3. The system of claim 1, wherein the probe is further configured to ultrasonically image the distal tip in real time.

4. The system of claim 3, further comprising a display configured to display real-time images of the global view.

5. The system of claim 4, wherein the display is further configured to display real-time images of the local view having a field of view that remains fixed with movement of the distal tip.

6. The system of claim 4, wherein the display is configured to display the global view and the local view simultaneously.

7. The system of claim 1, wherein the probe comprises a transesophageal (TEE) probe and the elongated instrument comprises a catheter.

8. The system of claim 1, wherein the echoic structure is hollowly annular and radially symmetric.

9. The system of claim 1, wherein the local viewing direction is longitudinally straight ahead from the distal tip.

10. The system of claim 1, wherein
the local view is formed from C-plane imaging and the processor is configured to reconstruct the local view in part by performing a coordinate system transformation of the subset of the volumetric data acquired by the probe to the local view.

* * * * *